Figure 1:
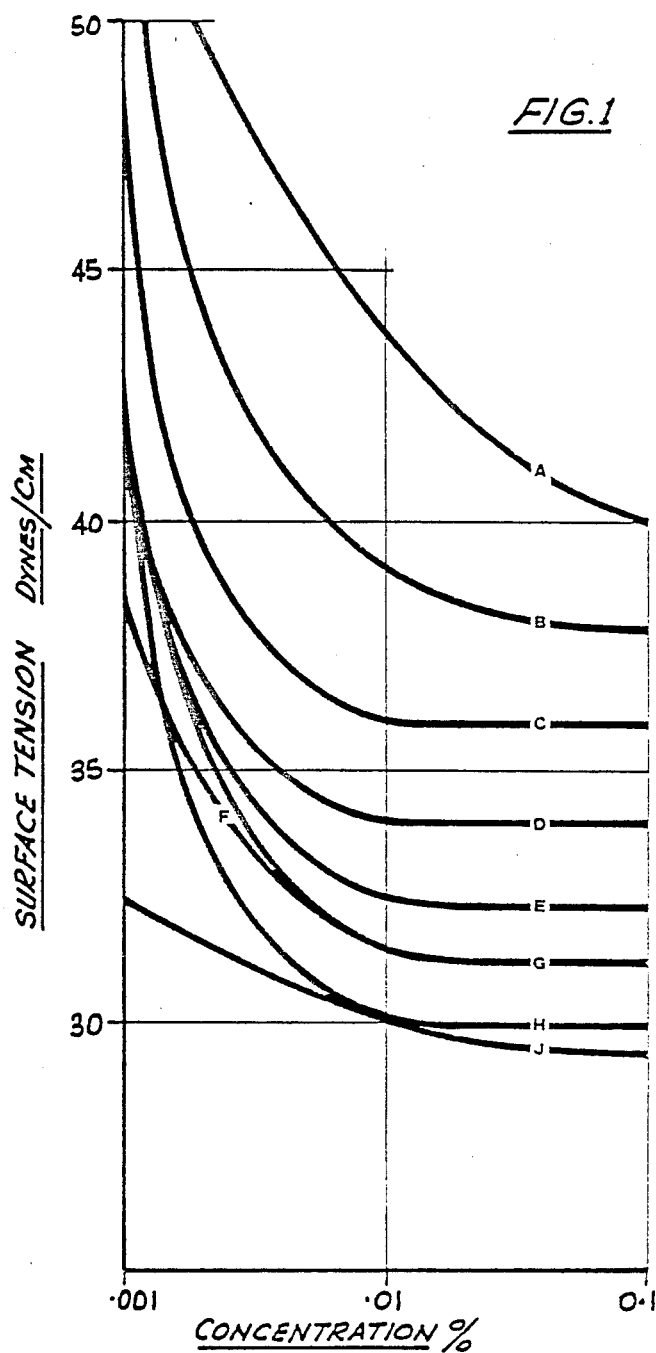

United States Patent [19]

Whiteley

[11] Patent Number: 4,748,279
[45] Date of Patent: May 31, 1988

[54] LIQUID STERILIZING COMPOSITION

[76] Inventor: Reginald K. Whiteley, 18 Glenside Street, Balgowlah Heights, N.S.W., Australia

[21] Appl. No.: 65,518

[22] Filed: Jun. 23, 1987

[30] Foreign Application Priority Data

Jun. 27, 1986 [AU] Australia ............................ PH6624

[51] Int. Cl.[4] ............................................. C07C 47/12
[52] U.S. Cl. ...................................... 568/494; 568/458; 568/460; 568/465; 525/501; 525/503
[58] Field of Search ............... 568/458, 460, 465, 494; 525/501, 503

[56] References Cited

U.S. PATENT DOCUMENTS

| 3,016,328 | 1/1962 | Pepper et al. | 167/22 |
| 3,282,775 | 11/1966 | Stonehill | 167/22 |
| 3,968,248 | 7/1976 | Boucher | 424/333 |
| 4,436,754 | 3/1984 | Jacobs | 424/333 |
| 4,448,977 | 5/1984 | Warner et al. | 549/201 |

FOREIGN PATENT DOCUMENTS

| 549358 | 2/1982 | Australia | 35/2 |
| 562017 | 6/1982 | Australia | 35/2 |
| 204717 | 6/1983 | New Zealand | 31/00 |
| 0878760 | 11/1981 | U.S.S.R. | 568/465 |

Primary Examiner—Werren B. Lone
Attorney, Agent, or Firm—Gausewitz, Carr & Rothenberg

[57] ABSTRACT

A liquid sterlizing composition comprising the reaction product of a non-ionic surfactant, a gluteraldehyde and triethylene glycol.

10 Claims, 3 Drawing Sheets

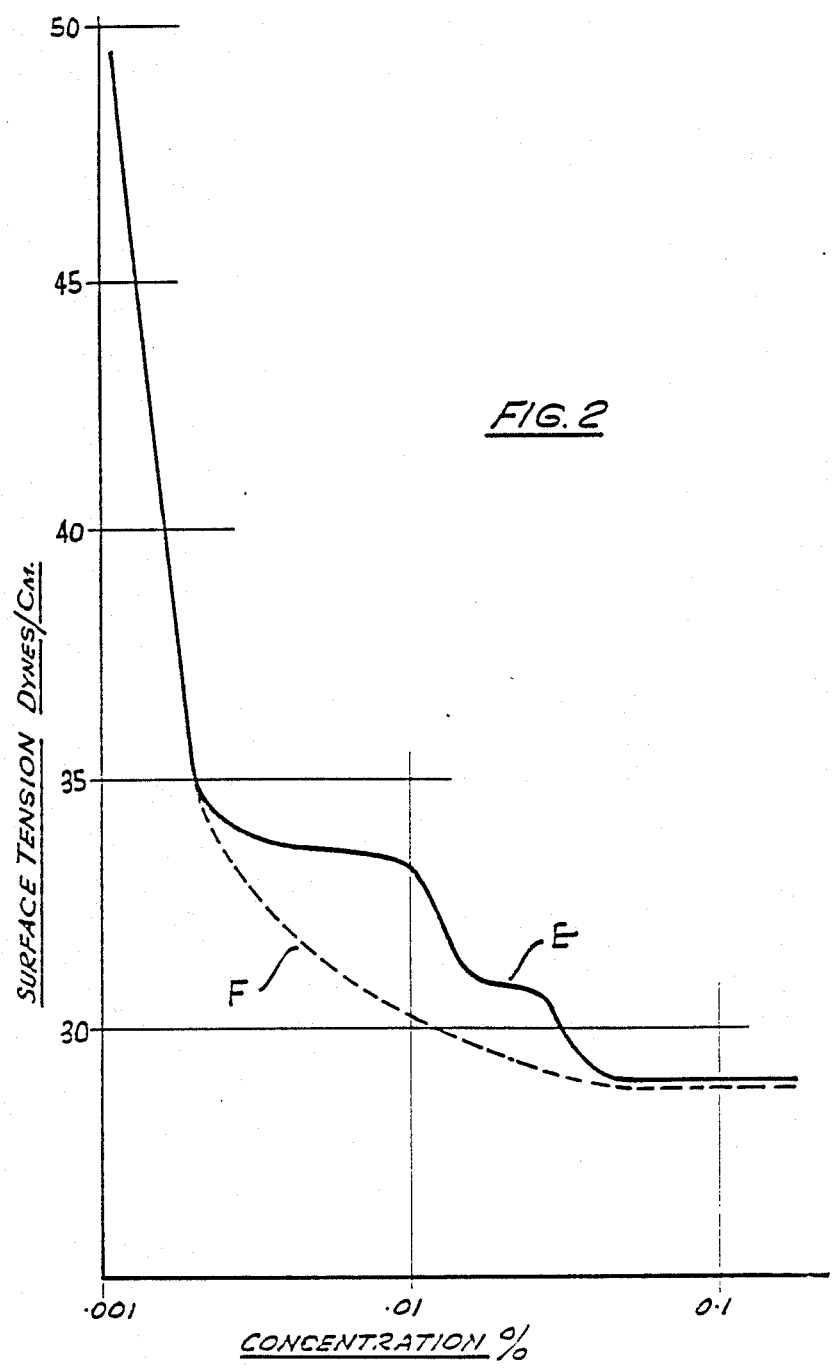

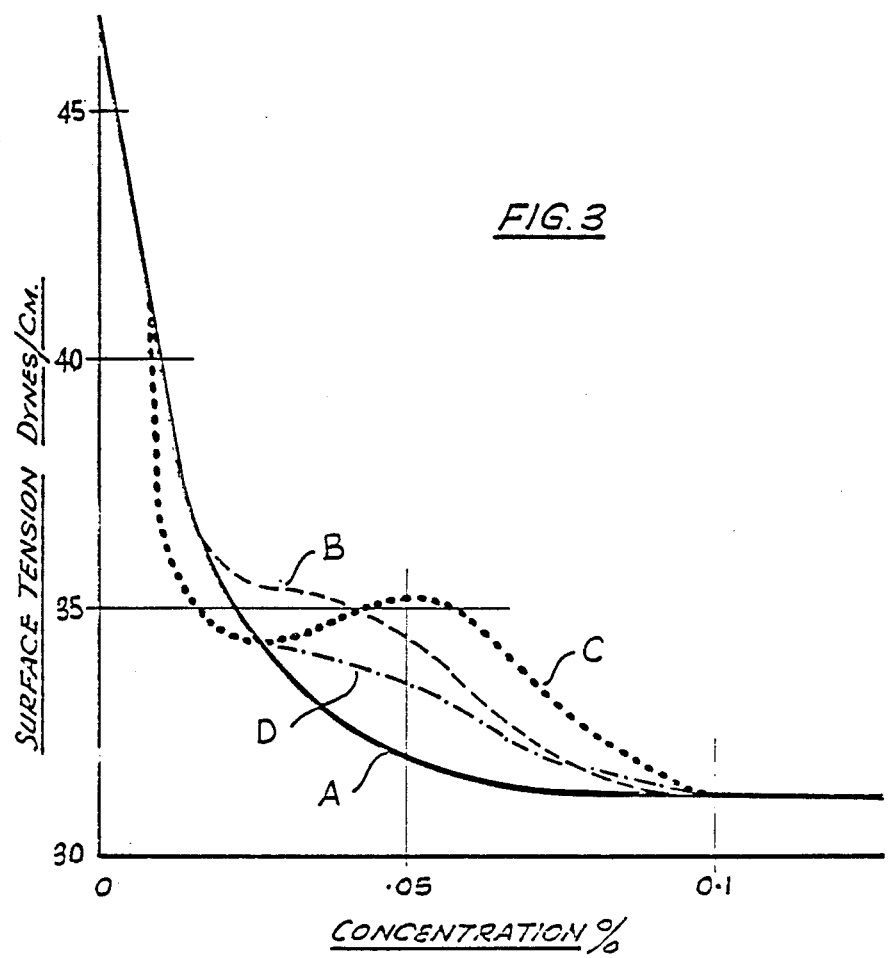

LIQUID STERILIZING COMPOSITION

This invention relates to a liquid sterilizing composition.

In the medical and health field there are any number of compositions which act as detergents, disinfectants and chemical sterilants. By dictionary definition "disinfecting" means to kill vegetative bacteria and other microorganisms whereas the term "sterilization" means total kill or destruction of not only bacteria, viruses and spores but all micro-biological organisms. Various chemicals and various combinations have been used as sterilants but in general they have practical disadvantages.

Of the sterilants currently acceptable in hospital, health care and general environmental hygiene, the practical choice currently lies between the following chemicals, each of which has quite serious occupational and health hazards when used under normal conditions for surface or immersion sterilisation.

Sodium hypochlorite:
Readily desctructive to skin tissue.
Highly toxic vapour (TLV value 1 ppm in air)
Highly irritant vapour.
Destructive to cellulosic and organic surfaces.
Highly corrosive to metals and work surfaces.
Glutaraldehyde
Readily attacks skin causing yellowing and progressive sensitisation.
Highly obnoxious and irritating vapour (TLV value 0.2 ppm in air. Irritation threshhold 0.1 ppm in air. Detection limit 0.04 ppm in air).
Highly allergy promoting when alkaline activated.
70% Ethanol/:
Highly inflammable.
70%:
Isopropanol Poor cleaning properties.
Progressive narcosis on inhalation.
Drying action of human skin.
Allergy promoting due to loss of skin constituents.
Peracetic Acid:
Poor cleaning properties.
Very strong vapour (ozone is emitted to air).
Vapour highly unpleasant and irritant.
Destructive to human skin above 0.25% oxidative acid.
Corrosive to metals due to acidic nature.

Clearly it will be seen that there is need for a product which will achieve the aim of adequate anti-viral and general biocidal activity whilst also being a generally useful sterilant without presenting the hazards now common to nurses and other hospital personnel who regularly use such products as part of normal infection control procedures.

Whiteley, R. K., Morgan, P. J. and Boucher, R. M. G. disclosed in New Zealand patent No. 204,717 and Australian patent No. 562,017 that reduced odour complexes could be formed with ethylene oxide derived glycols and glutaraldehyde by reaction at room temperature by a controlled process at an acidic pH and that the resultant product was both sporicidal, virucidal, bacteriocidal and tuberculocidal at pH 6.0–6.5. The resulting two-component complex was active and stable as a simple, ready-to-use product. A series of products based on this latter technology are now being marketed successfully for the sterilisation and disinfection of surgical instruments.

In the preceding two-component dialdehyde-glycol complexes surfactants were generally added. That the addition of surfactants into dilute (1-3%) glutaraldehyde solution accentuates biocidal action has been clearly demonstrated by prior art. Most commercial glutaraldehyde based chemical sterilants and high level disinfectants now contain either an anionic or nonionic surfactant for this reason and/or the ability of some surfactant to restrict the rate of polymerisation of monomeric glutaraldehyde in aqueous solution.

A study of the relationship of surface activity to the biological behaviour of glutaraldehyde-glycol complexes resulted in a number of very significant discoveries.

The first, and perhaps expected result, was that surfactants most efficient in reducing the air-water surface tension of the biocidal system gave products of maximum biocidal effectiveness. A surface tension of 30 dynes/cm or less was found desirable for optimum effectiveness.

From study of major groups of surfactants capable of reducing the air-water surface tension to 30 dyne/cm or lower it was found that low molecular weight nonionics, as typified by nonyl alcohol polyethoxylates, to be highly efficient. Other nonionic surfactants, including nonionic fluorocarbon surfactants, exert similar effect as do some amine oxide surfactants, typified by Ammonyx Co., manufactured by Onyx Chemical Corp., United States of America. It is practical to use nonionic surfactants in conjunction with anionic, amphoteric and cationic surfactants to achieve low surface tensions as well as to either increase the solubility of biocides and/or increase the cleaning ability of biocidal products manufactured in accordance with the disclosures herein.

Normally when a surfactant is added to a solution there is a lowering of surface tension which is directly proportional to the concentration of surfactant - until the "critical micelle concentration" (CMC) is reached. This is illustrated in FIG. 1 attached for eight commercial, nonionic surfactants manufactured by increasing the extent of ethoxylation of one mole of nonylphenol with from 5 to 30 mole of ethylene oxide surfactants.

The surfactants graphed in FIG. 1 are identified as follows:
A=Antarox, CO 880;
B=Antarox, CO 850;
C=Antarox, CO 730;
D=Antarox, CO 720;
E=Antarox, CO 710;
F=Antarox, CO 660;
G=Antarox, CO 630;
H=Antarox, CO 610;
J=Antarox, CO 520.

This shows the basic surface chemistry of non-ionic surfactants. When normal surfactants are added into either glutaraldehyde or a glutaraldehyde-glycol complex the surfactant exists in solution independently of and free from the other solution components; the surface tension of the solution is still directly proportional to the concentration of surfactant up to the CMC, according to classical theory.

This is the case in the solutions previously disclosed in patent literature including Australian patent No. 562,017.

The major discovery as herein described is that certain nonionic surfactants actually enter into reaction with glutaraldehyde and glycols to form new quite definite three-component reaction products which are considerably more biologically reactive than earlier two part dialdehyde-glycol complexes. This reaction occurs within a quite narrow composition range and its formation is limited to nonionic surfactants containing from 4 to 12 moles of ethylene oxide per nonionic molecule. The linear nonyl alcohol polyethoxylates, with from 4 to 10 moles of ethylene oxide as the hydrophile, are particularly effective in this regard. A commerical range of nonionic surfactants having this general composition are Teric 9A4, 9A5, 9A6, 9A8 and 9A10 manufactured by ICI Australia Ltd.

The particular novelty is that $C_9$ alcohol ethoxylates containing 4-7 units of ethylene oxide do not behave in this classical way.

Curve E of FIG. 2 shows the actual result whereas curve F illustrates the anticipated result using surfactant only.

TABLE 1 and FIG. 2 demonstrate this new invention. They clearly show that some of these surfactants enter into and become part of an inner biocidal complex in solution. Thus there is formed a 3-component complex—glutaraldehyde, glycol and surfactant—whereas all earlier disclosures were on either glutaraldehyde plus a surfactant or glutaraldehyde-glycol complex plus a surfactant each working independently in the final biocidal solution.

The three component reaction can be shown to occur with other nonionic surfactants, for example Tergitol 15-S-12 manufactured by Union Carbide Inc., United States of America. This is a $C_{15}$ secondary alcohol ethoxylate containing 12 moles of ethylene oxide. The phenomenon involved is best illustrated in the following TABLE 1 which shows reduction in the air-water surface tension of aqueous solutions of varying composition.

TABLE 1

| REDUCTION IN SURFACE TENSION | |
|---|---|
| Percentage Nonionic Surfactant | Air-Liquid surface tension at 20° C. |
| 0 | 63.0 dyne/cm |
| 0.01 | 40.5 dyne/cm |
| 0.02 | 34.0 dyne/cm |
| 0.03 | 33.7 dyne/cm |
| 0.04 | 33.7 dyne/cm |
| 0.05 | 33.2 dyne/cm |
| 0.06 | 31.0 dyne/cm |
| 0.07 | 31.0 dyne/cm |
| 0.08 | 29.0 dyne/cm |
| 0.10 | 29.0 dyne/cm |
| 0.20 | 28.8 dyne/cm |

The parameters of this reaction are clearly illustrated in FIG. 3.

A=surfactant only;
B=1.5 mole glycol per mole dialdehyde
C=1.0 mole glycol per mole dialdehyde
D=2.0 mole glycol per mole dialdehyde This clearly demonstrates that when the mole ratio of glutaraldehyde to triethylene glycol is in the range 1:1 to 1:1.5 there is loss of the surfactant from the aqueous solution into a chemical compound. Whereas the surface tension of these solutions should fall in direct proportion to the concentration of surfactant, up to the Critical Micelle Concentration, it is noted that there is an unexpected change in shape of the curve. The shape of the curve, which demonstrates loss by reaction of surfactant from the solution, depends on the ratio of glutaraldehyde to triethylene glycol. It will be noted that the optimum ratio of glutaraldehye to triethylene glycol is 1:1.5. A similar phenomenon is observed with diethylene glycol.

The composition formed in this reaction, while not positively identified, is most likely a hydrogen bonded surface active polymer containing in general order of arrangement glycol-dialdehyde-glycolnonionic sufactant-dialdehyde, etc. or combinations thereof. The presence of the hydrophobe of the surfactant in the polymer may well contribute to greatly increased interfacial availability of the dialdehyde at a concentration and in a form in which it is both more biologically reactive and more stable than earlier forms of glutaraldehyde biocides. Clearly bond strengths within the polymer and the positioning of the carbonyl groups therein is such as to facilitate its reactivity at the biological interface.

It was also found that some other biocidal compounds could additionally be incorporated into these new reaction products once the initial reaction just described had occurred. Notable in this regard were amine and cationic biocides. Both simple and substituted phenols, as typified by dimethyl phenols and closely related isomers boiling in the range 210°-235° C., either alone or in combination with chlorinated phenols such as parachlormetaxylenol (PCMX), could also be solubilised into these latter reaction products. In each case an increase occurred in the anti-microbial activity of the resulting aqueous complex over that expected of the respective biocides when formulated as normal single component commercial disinfectants.

From a study of the chemical stability of these latter phenolic solutions it was found that simple phenols and alkyl substituted phenols yielded biocidal products in which the availability of monomeric glutaraldehyde (determined by classical titration method) remained essentially constant over long periods.

Initial study of the antimicrobial activities of these new multicomponent biocidal solutions centered upon the organism *Pseudomonas Aeruginosa* NCTC 6749, using the protocol of the T.G.A. Disinfectant Test, Option B (B. M. Graham 1978, Aust. Journal Hosp. Pharm: Vol 8, No. 4, p.149-155).

The organism had previously been shown to be the more resistant to glutaraldehyde of the four organisms employed in the particular protocol. Results were compared with the commercial product WAVICIDE-AID conforming to the Australian patent No. 562,017 of Whiteley et al.

The following are examples of multi-component mixtures which can interact to form strongly biocidal preparations with the parameters of this invention.

EXAMPLE 1

Ready-to-use Chemical Sterilant

Mix in order listed the following ingredients:

| | |
|---|---|
| 25% medical grade glutaraldehyde | 6.0 gram |
| Triethylene glycol | 6.0 gram |
| Teric 9A6 (ICI AUST. P/L) | 0.20 gram |
| Stand for 30 minutes, at pH 4.5-5.5 then add | |
| Sodium phosphates buffer (to pH 6.3-6.5) | 0.2 gram |
| Water to | 100 gram |
| Adjust pH to 6.3-7.0 with sodium phosphate buffer. | |

EXAMPLE 2

A dilutable quaternary containing complex made by mixing in order:

| | |
|---|---|
| 25% medical grade glutaraldehyde | 20.0 gram |
| Triethylene glycol | 25.5 gram |
| Teric 9A6 (ICI AUST. P/L) | 1.5 gram |
| Stand for 30 minutes, then add: | |
| Gardiquat 12-H (50% active) (Albright & Wilson) | 20.0 gram |
| Demineralised Water | 30.75 gram |
| Ethylene diamine tetra acetic acid | 2.0 gram |
| Sodium phosphates buffer (to pH 6.3–7.0) | 0.25 gram |

The minimum concentrations of glutaraldehyde found to give consistently reproducible results Ps. aeruginosa NCTC 6749 are as follows:

| | |
|---|---|
| WAVICIDE-AID | 0.33% glutaraldehyde (as reactive monomer) |
| EXAMPLE 1 | 0.25% glutaraldehyde (as reactive monomer) |

There is a demonstrable and biologically significant increase in the effectiveness of the three component reaction product.

This finding was further verified using a much more chemically resistant mycobacterium bovis. The two products, WAVICIDE AID and EXAMPLE 1, when tested by the AOAC protocol against a quite resistant wild New Zealand strain of *M. tuberculosis* gave results as follows on samples of each product one month old.

TABLE I
BIOCIDAL PERFORMANCE AGAINST M. TUBERCULOSIS

| Product | Solution Temp. | Exposure Time to biocide in minutes | | | | | |
|---|---|---|---|---|---|---|---|
| | | 5 | 10 | 15 | 20 | 30 | 60 |
| WAVICIDE-AID | 14° C. | G | G | G | G | G | G |
| | 20° C. | G | G | G | G | G | G |
| | 25° C. | G | NG | NG | NG | NG | NG |
| EXAMPLE 1 | 14° C. | G | G | NG | G | NG | NG |
| | 20° C. | NG | NG | NG | NG | NG | NG |
| | 25° C. | NG | NG | NG | NG | NG | NG |

G = growth on culture plate after 42 days at 37° C.
NG = no growth after 42 days at 37° C.

The improved three component product represented by EXAMPLE 1 clearly demonstrates very significant improvement in mycobactericidal action. Cell inactivation and/or cell death of the mycobacterium also occur quite quickly (5 minutes or less) which is important when the preferred normal exposure time for disinfecting surgical instruments must now be 10 minutes minimum to ensure adequate biocidal action. EXAMPLE 1 is therefore eminently suitable as a surgical instrument disinfectant when mycobacterium may be encountered. As virucidal action against small non-enveloped viruses such as Hepatitis B and human Rotaviruses has been shown to be closely linked to mycobactericidal performance ("Morbidity and Mortality Weekly Report", Nov. 15, 1985, Vol. 34/No.45) this latter finding on kill rate assumes even greater practical significance.

A still further benefit of the compositions disclosed herein is the ability to achieve total elimination of the obnoxious odour from both dilutable concentrates and ready-to-use biocidal solutions containing glutaraldehyde. This latter phenomenon is pronounced when either an n-alkyl dimethyl or ethyl benzyl ammonium chloride is incorporated into a nonionic-glycol-glutaraldehyde complex after initial reaction. Indeed, the phenomenon is general to cationic biocides. EXAMPLE 2 is such a composition.

Despite the total loss of odour (by total reaction of glutaraldehyde in EXAMPLE 2) there is, as previously mentioned, demonstrable increase in the ability of this biocide to combine with reactive sites on smaller more chemically resistant viruses, in particular Hepatitis B (HBV).

What seems most significant, and indeed may well represent a new disclosure in biocidal mechanisms, is that the surface activity of the reaction complex formed in EXAMPLE 2 increases its ability to reduce the activity of the HBsAg, the surface antigen of HBV. The reaction complex appears to be an efficient vehicle for transporting biocide either singly or in combination to the surface of microbes. Increased cidal activity to small non-capsulated chemical resistant viruses, like HBV which are amongst the most difficult to inactivate to kill by chemical means, has been clearly demonstrated.

EXAMPLE 3

A dilutable phenolic containing complex made by mixing in order:

| | |
|---|---|
| Dimethyl phenols (BP 210–235° C.) | 15.0 gram |
| Isopropanol | 5.0 gram |
| Triethylene glycol | 15.0 gram |
| Sodium linear dodecyl benzene sulphonate (100% active) | 2.5 gram |
| Teric 9A5 | 1.5 gram |
| Mix to a clear solution then add | 10.0 gram |
| 50% medical grade glutaraldehyde | |
| Water, Demineralised | 49.0 gram |
| (Allow to stand for 30 minutes) | |
| Ethylene diamine tetra acetic acid | 2.0% |
| Potassium hydroxide, 50% soln. to pH | 6.3–7.0 |

Increase in biocidal activity of a glutaraldehyde-glycol-nonionic reaction product containing a second biocide is further illustrated in the case of EXAMPLE 3. Here the full protocol of the T.G.A. Disinfectant Test, Option B, was employed to determine the minimum concentration of biocide needed to pass this particularly rigorous test. The results are documented in the following table.

TABLE III
PERCENTAGE ACTIVE BIOCIDES TO PASS TGA DISINFECTANT TEST. OPTION B

| | S. aureus NCTC 4163 | P. vulgaris NCTC 4634 | E. Coli NCTC 8196 | Ps. aeruginosa NCTC 6749 |
|---|---|---|---|---|
| GLUTARALDEHYDE (pH 6.3) | 0.25 | 0.25 | 0.25 | 0.33 |
| DIMETHYL PHENOLS | 0.40 | 0.35 | 0.35 | 0.35 |
| BENZALKONIUM CHLORIDE BP | 0.25 | 0.30 | 0.30 | 0.35 |
| WAVICIDE AID | 0.25 | 0.25 | 0.25 | 0.33 |
| EXAMPLE 1 | 0.20 | 0.20 | 0.20 | 0.25 |
| EXAMPLE 2 | 0.17 | 0.16 | 0.20 | 0.15 |
| EXAMPLE 3 | 0.17 | 0.17 | 0.20 | 0.18 |

Again the increase in total microbial performance is clearly demonstrated. EXAMPLE 3, for example, is entirely suitable as a practical high level hospital disinfectant. It has a mild, slightly sweetish phenolic odour characteristic of the dimethyl phenol used in its preparation and superior cleaning properties.

A further significant observation of the aqueous complex illustrated by EXAMPLES 1, 2 and 3 is that they are able to associate in stable form with some other surfactants. However, the association is charge specific. For example, a highly water soluble anionic surfactant sodium dodecyl sulphate is slowly precipitated on standing when mixed into EXAMPLE 1. Likewise, phosphated alkyl phenol polyethoxylates form a separate liquid phase on standing. However, many alkyl phenol polyethoxylates, linear alcohol polyethoxylates, amine oxides, alkyl benzene sulphonates, amphoteric and nonionic fluorcarbon surfactants can successfully be incorporated into these three components reaction complexes if required.

There is advantage in also incorporating into chemical sterilants and biocides small quantities of organic chelating agents such as ethylene diamine tetracetic acid and nitrilo triacetic acids and their soluble salts, both of which aid in the destruction of many gram negative bacteria. Also included may be a dilute sodium or potassium phosphate buffer to regulate pH plus a corrosion inhibitor such as sodium nitrite. Acidic zinc phosphate can also be used to protect steels. A stabiliser of a phenolic type can also be incorporated as well as dyes and perfumes which are compatible with the principal chemical complex in the chemical sterilant.

The teachings of this patent permit the formulation of marketable products which may be sold either as concentrates, to be later diluted with either potable water or an alcohol or mixtures thereof, or alternatively packaged in ready-to-use form. Typically concentrated products may contain from 2.5 to 60 per cent by weight of active biocides whereas ready-to-use products may contain from 0.1 to 3.5 per cent active biocides depending upon the particular use of the product and the overall biocidal effectiveness required for the relevant end use.

As will be seen these EXAMPLES constitute new and novel improvements on existing dialdehyde biocides. They offer wide safe use in medicine, dentistry, veterinary practical, pharmacy and pharmaceutical manufacture, horticulture, biogenetic engineering, food poroduction and processes, first aid, safety procedures, and general public and private hygiene.

These are especially important and constitute new developments in the systems and methods available for control of the spread of HIV (Human Immunosuppresive Virus) HTLV III, the products for the disinfection of which largely mimic those normally employed for the environmental control of Hepatitis B (HBV).

The foregoing examples of a sterilising composition are made by reacting together in aqueous solution at ambient temperature at pH 4.0–6.0:

(a) Glutaraldehyde, medical grade, in the proportion of 0.05 to 30 per cent in the final product.

(b) Triethylene glycol in mole ratio of 0.5 to 2.0 mole (preferably 1.0 to 1.5) of glycol per mole of glutaraldehyde.

(c) A nonionic surface active agent containing from 4 to 12 mole of ethylene oxide in the proportion of 0.02 to 20.0 per cent of the final product. These ingredients are allowed to react to 20 to 30 minutes at ambient temperature after which may be added as desired:

(d) A quaternary amine biocide chosen from the group of alkyl dimethyl, di ethyl or methyl ethyl or benzyl ammonium halides in the proportion of 0.005 to 30 per cent in the final product, or alternatively (e) A phenolic biocide chosen from the group, phenol, ortho, meta and para cresols, dimethyl phenols and analogues boiling in the range 210°–235° C., monochlor-xylenol, parachlormetaxylenol (PCMX) and dichlormeta-xylenol (DCMX) in the proportion of 0.1 to 15.0 per cent of the final product.

(f) An organic chelating agent, for example ethylene diamine tetracetic acid di or trisodium salt, in the proportion 0.05 to 7.5 per cent of the final product.

(g) A perfume compatible with the above biocides, for example Citral, in the proportion 0.01 to 1.0% of the final prepararion.

(h) An alcohol which may be either etanol or ispropanol or mixtures thereof in the proportion of 5 to 80 per cent of the final composition.

(i) The pH is adjusted from 4.5 to 7.2, (preferably 6.0–6.5), by the use of a mon-valent alkali preferably sodium.

The surfactant is preferably chosen from an alcohol polyglycol containing 4 to 12 ethylene oxide groups reacted on to a linear alcohol comprising 7 to 18 carbon atoms, or an alkyl or dialkyl phenol (the alkyl group containing 4–12 carbon atoms) reacted with 4 to 15 ethylene oxide groups.

The dialdehyde which may be chosen from the group glyoxal, glutaraldehyde, 1 succindialdehyde or other mono or dialdehyde which has been shown to kill Hepatitis B (HBV) at a concentration below 15.0% by weight in an aqueous solution at a pH of 4.5–7.5.

The organic chelating agent may be a di, tri or tetra carboxy acid derivative of a mono or diamine or tetra or nitrilo triacetic acid which has the identifiable property of being able to react with and/or leach from virucidal or bacterial cells traces of divalent metals which are essential to microbviological reproduction processes.

An alcohol solvent being either ethanol or ispropanol.

A glycol which may be either diethylene glycol, triethylene glycol, tetra ethylene glycol, the mono methyl ether of di, tri or tetra ethylene glycol or polyethylene condensates with a maximum molecular weight of 800.

Phenol, cresols or dimethyl phenols in the boiling point range 205° C.–230° C. and/or simple chlorinated alkyl phenols; alternatively by an efficient quaternary amine biocide which group includes chlorhexidine derivates in the proportion 0.1 to 25.0 per cent of the final product.

It will benoted that these various mixtures have in common a dialdehyde, preferably glutaraldehyde, a glycol derived from ethylene oxide and a nonionic surfactant preferably one which will yield a surface tension of 30 dyne/cm or less in either aqueous or alcoholic solution at the final use strength of the biocidal formulation.

To suit specific needs, a second, third and even fourth known biocide chosen from the groups of quaternary amine, cationic or substituted phenols may be added, plus an efficient chelating agent and a buffer system to regular pH. A corrosion inhibitor such as sodium nitrite, a perfume and dye can be added to complete a product if so desired.

The formulations envisages in this disclosure have a pH of 4.5 to 7.2. Whereas glutaraldehyde is relatively stable in acidic solutions it readily polymerises in alkaline solution; however, it exhibits maximum virucidal effectiveness in the pH range 6.3 to 7.2. It is therefore desirable that a concentrated disinfectant containing glutaraldehyde be chemically stable and yet yield a pH of 6.3 to 7.2 when diluted ready-for-use with tap water.

I claim:

1. A compound for liquid sterilizing compositions comprising the product made by simultaneously reacting
    (a) a nonionic surfactant containing from 4 to 12 moles of ethylene oxide per nonionic molecule with
    (b) glutaraldehyde and triethylene glycol in a mole ratio of from 2.0 to 0.5 to 1.0 to 1.75 respectively for a period of from 20 to 30 minutes at ambient temperature and at a pH of from 4.0 to 5.5.

2. The compound of claim 1 wherein said nonionic surfactant is a linear nonyl alcohol polyethoxylate containing from 4 to 10 moles of ethylene oxide.

3. The compound of claim 1 wherein said nonionic surfactant is a $C_9$ alcohol ethoxylate containing from 4 to 7 moles of ethylene oxide.

4. The compound of claim 1 wherein said nonionic surfactant is a $C_{15}$ secondary alcohol ethoxylate containing 12 moles of ethylene oxide.

5. The compound of claim 1 wherein the mole ratio of said gluteraldehyde to triethylene glycol is in the range of 1:1 to 1:1.5.

6. The compound of any one of the foregoing claims wherein the nonionic surfactant is in the proportion of 0.02 to 20.0 per cent by weight of the total compound.

7. The compound of any one of the foregoing claims wherein the reaction takes place over a period of from 20 to 30 minutes at ambient temperature.

8. The compound of claim 1 wherein said nonionic surfactant is an alcohol polyglycol containing 4 to 12 ethylene oxide groups reacted onto a linear alcohol containing 7 to 18 carbon atoms.

9. The compound of claim 1 wherein said nonionic surfactant is an alkyl or dialkyl phenol containing 4 to 12 carbon atoms reacted with 4 to 15 ethylene oxide groups.

10. A method of making a compound for liquid sterilizing compositions comprising the steps of mixing together:
    (a) a nonionic surfactant containing ethylene oxide with
    (b) 1.0 to 1.5 moles of glutaraldehyde and
    (c) 1.0 to 1.5 moles of triethylene glucol and reacting the foregoing compounds a, b, and c for a period of from 20 to 30 minutes at ambient temperature.

* * * * *